US009314747B2

(12) United States Patent
King et al.

(10) Patent No.: US 9,314,747 B2
(45) Date of Patent: Apr. 19, 2016

(54) CARTRIDGES FOR BULK FEEDERS (75) Inventors: Joseph A King, Wayzata, MN (US);
Jeffrey D Johnson, Edina, MN (US)

(73) Assignee: KING TECHNOLOGY, INC., Hopkins, MN (US)

( * ) Notice: Subject to any disclaimer, the term of this patent is extended or adjusted under 35 U.S.C. 154(b) by 641 days.

(21) Appl. No.: 13/573,021

(22) Filed: Aug. 14, 2012

(65) Prior Publication Data

US 2013/0098820 A1    Apr. 25, 2013

Related U.S. Application Data (60) Provisional application No. 61/628,096, filed on Oct. 24, 2011.

(51) Int. Cl.
| | |
|---|---|
| *B01D 11/02* | (2006.01) |
| *B01F 1/00* | (2006.01) |
| *C02F 1/68* | (2006.01) |
| *B01F 5/04* | (2006.01) |
| *A61L 2/23* | (2006.01) |
| *A61L 2/238* | (2006.01) |
| *C02F 1/50* | (2006.01) |
| *C02F 1/76* | (2006.01) |
| *C02F 103/42* | (2006.01) |
| *E04H 4/12* | (2006.01) |

(52) U.S. Cl.
CPC ............. *B01F 1/0027* (2013.01); *A61L 2/23* (2013.01); *A61L 2/238* (2013.01); *B01F 5/0496* (2013.01); *C02F 1/688* (2013.01); *B01D 11/0215* (2013.01); *B01D 11/0219* (2013.01); *C02F 1/505* (2013.01); *C02F 1/76* (2013.01); *C02F 1/766* (2013.01); *C02F 2103/42* (2013.01); *C02F 2201/004* (2013.01); *C02F 2201/006* (2013.01); *C02F 2201/007* (2013.01); *C02F 2209/29* (2013.01); *C02F 2209/40* (2013.01); *C02F 2303/04* (2013.01); *E04H 4/1281* (2013.01); *Y10T 29/49716* (2015.01)

(58) Field of Classification Search
CPC ................. B01F 1/0027; B01F 5/0496; Y10T 29/49716; C02F 1/505; C02F 1/688; C02F 1/76; C02F 2103/42; C02F 2201/006; C02F 2303/04; C02F 1/766; C02F 2201/004; C02F 2201/007; C02F 2209/29; C02F 2209/40; A61L 2/23; A61L 2/238; E04H 4/1281; B01D 11/0215; B01D 11/0219; B01D 11/0223
USPC .............. 210/335, 198.1, 200, 201, 202, 205, 210/167.11; 422/261, 275, 276, 277, 278
See application file for complete search history.

(56) References Cited

U.S. PATENT DOCUMENTS

| | | | |
|---|---|---|---|
| 5,251,656 A | 10/1993 | Sexton, Sr. | |
| 6,383,382 B1 * | 5/2002 | Johll et al. | 210/266 |
| 7,658,844 B2 * | 2/2010 | Blanchette | 210/198.1 |
| 2005/0242016 A1 | 11/2005 | King | |
| 2008/0296214 A1 * | 12/2008 | Blanchette | 210/198.1 |

FOREIGN PATENT DOCUMENTS

EP         0352355         1/1990

* cited by examiner

*Primary Examiner* — Fred Prince
(74) *Attorney, Agent, or Firm* — Jacobson & Johnson LLC

(57) ABSTRACT

A cartridge system for converting a bulk feeder which delivers a single water treatment material at a high rate to a bulk feeder that delivers two or more water treatment materials at a lower rate through locating a set of dispensing cartridges in the chamber of the bulk feeder with the dispensing cartridges held in position to maintain the fluid outlet port of one of the cartridges in fluid alignment with the fluid inlet port of another cartridge to provide cartridge to cartridge flow without having to circulate the fluid through the chamber of the bulk feeder.

26 Claims, 6 Drawing Sheets

CARTRIDGES FOR BULK FEEDERS

CROSS REFERENCE TO RELATED APPLICATIONS

This application claims priority from U.S. provisional application Ser. No. 61/628,096 filed Oct. 24, 2011.

STATEMENT REGARDING FEDERALLY SPONSORED RESEARCH OR DEVELOPMENT

None

REFERENCE TO A MICROFICHE APPENDIX

None

BACKGROUND OF THE INVENTION

This invention relates generally to dispensing cartridges and, more specifically, to an interactive cartridge system having a plurality of dispensing cartridges for placement in a bulk feeder to enhance the delivery and enhance the control of the delivery of water treatment materials from the bulk feeder through establishment of serial flow from cartridge to cartridge within the bulk feeder.

One of the ways of ridding pools, spas or other bodies of water of harmful organism is to add a halogen such as chlorine or bromine to the body of water. Typically, the halogen may be added to the body of water through a bulk feeder. In the bulk feeder tablets or pucks of chlorine or bromine are placed in a chamber of the bulk feeder where the water flowing through the bulk feeder comes into contact with the halogen located therein. One of the disadvantages of the bulk feeders is that it is difficult to control the level of halogen that is dispersed into the body of water, which often results in over chlorination or over brominating of the body of water. While such bulk feeders are relatively inexpensive the cost of the overuse of chlorine and or bromine in the bulk feeders can quickly negate any benefits of the bulk feeder. To reduce the problem of over chlorination or bromination as well as improving the control of the level of chlorine or bromine in a body of water other types of feeders that separately dispense two different biocides may be used.

One prior art method and apparatus for controlling the harmful organisms in a body of water in a bulk feeder uses two non-fitted dispensers that deliver two different biocides through the establishment of random flow of water through each of the dispensers. Such a device is shown in King U.S. Pat. No. 7,347,935. In this device the two biocides are located in two separate dispensers that are placed in a free or non-fitted condition in the chamber of a bulk feeder. The two dispensers are allowed to move or tumble about in the chamber in response to the fluid flow through the chamber of the feeder, which enables the water in the chamber to come into contact with the biocides located therein. As the dispensers move about in the chamber of the feeder the biocides therein are released into the water passing through the chamber of the feeder. In such devices in addition to the control valve on the feeder, which limits the flow of water into the chamber, the dispensers include adjustable valves on each dispenser in order to better control the dispersant level of each of the biocides.

Another chemical feeder for dispensing two chemicals into a pool is shown in U.S. Pat. No. 5,251,656 where two compartments containing water treatment materials with a venturi housing to draw the water treatment materials out of each of the compartments and into the pool.

U.S. Pat. No. 6,471,858 shows a dispensing apparatus where a pair of cylindrical containers containing water treatment materials are located in a coaxial condition. The containers are cantileverly mounted within a top chamber in a sand filter, which allows the water to flow through both of the containers before flowing through a bed of sand.

A method and apparatus for accurately delivering two biocides from a single chamber in an inline feeder is shown in King U.S. Pat. Nos. 6,527,952 and 6,190,547. In this device two nestable canisters are concentrically positioned in the chamber of an inline feeder with each of the nestable canisters having inlets and outlets that separate or bifurcate the flow of water into two separate streams with each of the two streams following separate but parallel flow paths through the biocides in their respective nestable canisters.

Since most feeders are integrally mounted in a circulation line of a body of water such as a pool or spa the conversion of a bulk feeder to a cartridge system that can accurately deliver two different biocides becomes costly since one may have to remove and replace the existing bulk feeder with a feeder that provides parallel flow paths through the dispensers therein. In other cases where the dispensers are free to move about the chamber of the feeder the task of control of the delivery rate of the biocides from the separate dispensers becomes more delicate since in addition to adjusting the setting of the control valve of the bulk feeder the valve of one or both of the dispensers may need to be adjusted periodically to control the flow of water through the dispensers and hence the level of biocide that is delivered to the body of water. Thus, a need exists for a cartridge system that can be used in prior art bulk feeders to alleviate problems of over halogenation as well as provide a system that can precisely deliver two or more water treatment materials to the body of water, which for example may be a pool, a spa or the like although the cartridge system may be used with any body of water which requires delivery of water treatment materials thereto.

In contrast to the prior art, the invention described herein allows one to provide enhanced dispersant control using the existing valve controls and without modifications thereof.

SUMMARY OF THE INVENTION

Briefly, the invention comprises a set of dispensing cartridges that can be placed in a side-by-side condition in a chamber of a bulk feeder, which is attached to a main line, with the fluid outlet port of one of the dispensing cartridge in fluid alignment with the fluid inlet port of an adjacent dispensing cartridges to provide serial flow from cartridge to cartridge. Each of the dispensing cartridges have at least one feature for directly indirectly engaging with a feature in the bulk feeder or to each other to maintain the dispensing cartridge in a static condition with respect to the bulk feeder. The bulk feeders, which include a control valve having a variable opening for directing water into the chamber is used to control the flow of water through the serially arranged dispensing cartridges. The serial arranged cartridges dispense the materials at a lower rate than a bulk dispenser with bulk water treatment materials therein. As the dispensing cartridges are serially maintained in a direct line of flow in the chamber of the bulk feeder the serially arranged dispensing cartridges and the contents therein coact to limit the dispersing rate of materials therefrom enabling one to use the existing water control valves on the bulk feeder to dispense material at rates which are less than those rates normally obtainable when only a bulk material is located in the chamber of the bulk feeder. Consequently, not only can the existing valve in the bulk feeder be used to control the delivery of water treatment materials the serial arrangement of the dispensing cartridge provides enhanced control of the delivery rates of two or more water treatment materials with the further benefit of preventing or inhibiting over halogenation that normally occurs in bulk feeders that contain only a halogen therein.

DESCRIPTION OF THE PREFERRED EMBODIMENT

Figure 1:
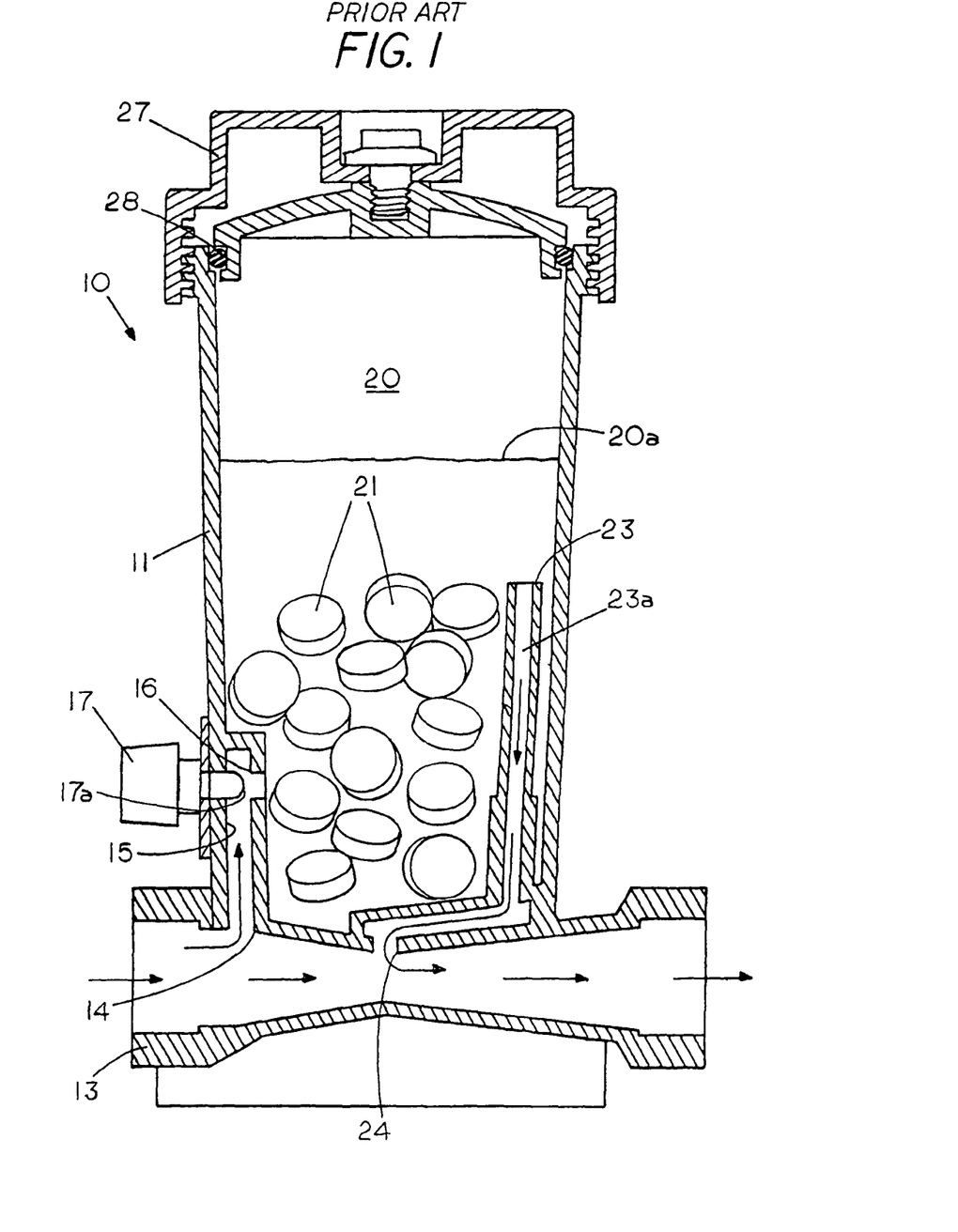
FIG. 1 shows in cross section an example of a prior art bulk halogen feeder.

FIG. 1 shows a typical example of a prior art bulk halogen feeder 10, which is sold by Hayward Industries, Inc., having a frusto conical housing 11 with a lower venturi 13 having an inlet 14 for directing a portion of the water flowing therethrough into a channel 15 and through a passage 16 and into chamber 20 where the water contacts the halogen 21, which is in bulk form and is shown located below the water line 20a in the chamber 20. In this example a rotateable control valve 17 allows one to increase or decrease the amount of water flowing into chamber 20 and consequently into contact with the bulk chlorine tablets 21 by reducing or increasing the spacing between valve end 17a and passage 16. Once the water contacts the halogen tablets 21 the water can flow out of chamber 20 through a fluid passage 23a in a vertical stand tube 23 and back into the venturi 13 through the port 24. A cover 27, which is sealed to the housing 11 through an annular seal 28, normally maintains the bulk feeder in a closed condition when the system is in use. It is this type of bulk feeder that is prone to over halogenation as the water flows freely through the halogen tablets 21 before being discharged through the stand tube 23.

Figures 2, 2A:
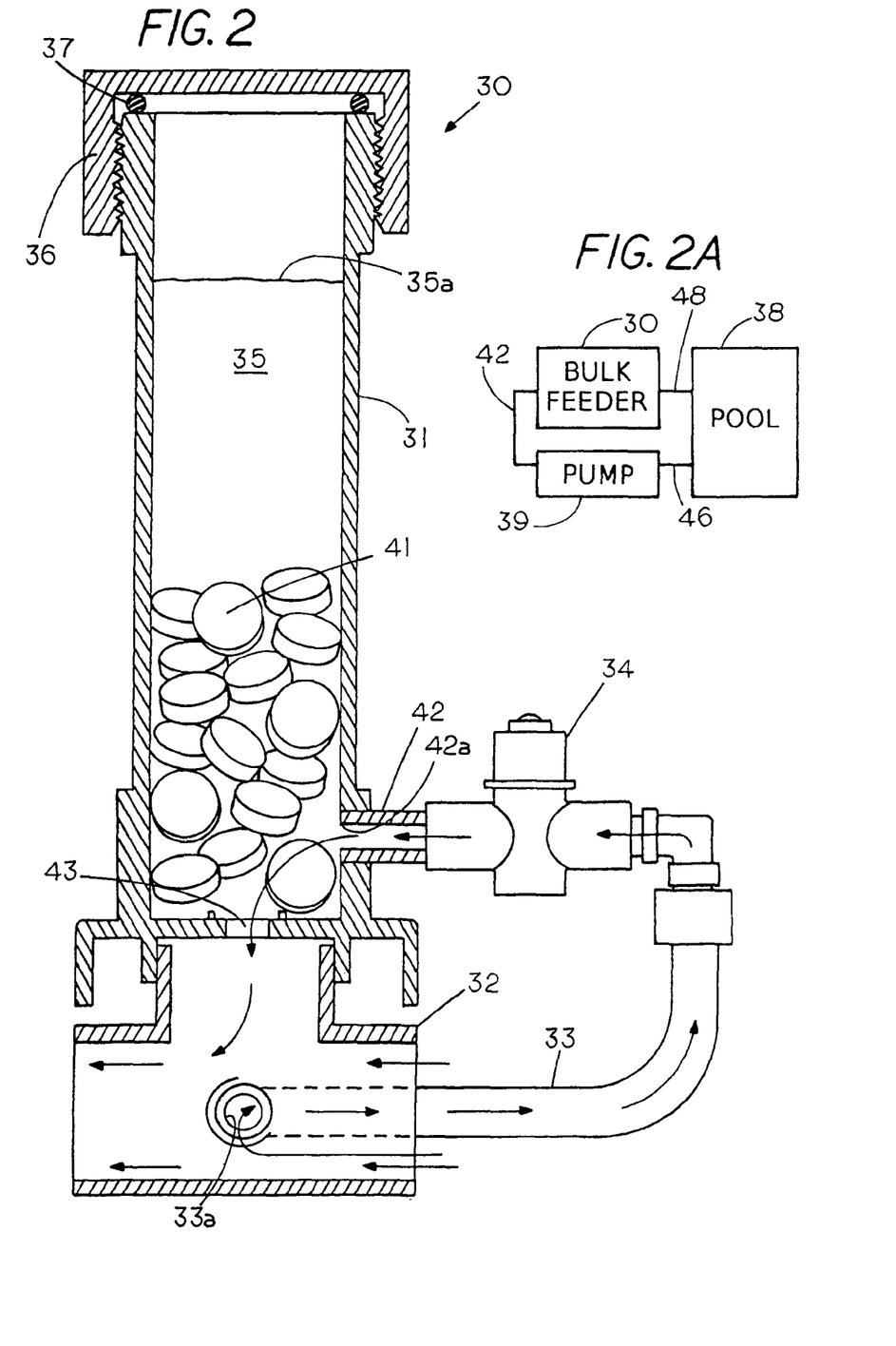
FIG. 2 shows cross section an example of another type of prior art bulk halogen feeder.
FIG. 2A shows a swimming pool with a bulk feeder.

FIG. 2 shows another typical example of a prior art bulk halogen feeder 30, which is sold by Rainbow Lifeguard Products, Inc., having a cylindrical housing 31 with a lower main line fitting 32 which attaches to an inline circulating system. A side tap 33a directs a portion of the water from the main line fitting 32 through a pipe 33 to a control valve 34, which can be used to limit the flow of water from the main line through the chamber 35. The housing includes a cover 36 and an annular seal 37, which creates an airtight chamber 35. In operation a portion the water flowing through the main line fitting 32 flows into side tap 33a through pipe 33, control valve 34, pipe 42 and inlet 42a where it can then flow through the bulk chlorine tablets 41, which are located below the water line 35a in chamber 35. The water with the dissolved halogen therein then flows out of the chamber 35 through outlet 43 and into the fitting 32 where it is returned to the main inline circulation system. This type of system has also been found to become over halogenated since the halogen tablets 41 are rapidly dissolved by the water flowing through the open chamber 35.

Briefly, in the above type of systems the halogen in puck or tablet form is located in the chamber of the bulk feeder while one attempts to control the release of the halogen therefrom by using a flow valve on the feeder to direct more or less water through the chamber containing the bulk halogen tablets, which are stacked loosely and randomly in the chamber of the bulk feeder. Unfortunately, the accurate and controlled delivery of halogen to the body of water becomes difficult when the tablets or pucks are located in the chamber in the bulk feeder since the delivery rate is sensitive to the variable resistance offered by the dissolvable halogen pucks or tablets as well as the number tablets or pucks that are located below the water line 35a. Because of the difficulty in accurately delivering the proper amount of halogen through bulk feeders such as described an operator may want to ensure that a minimum amount of halogen is always available in the water, which may result in valve settings on the feeder that causes over halogenation i.e. over chlorination or over bromination of the body of water. The above are two examples of bulk halogen feeders that are prone to over halogenation, however, other types of bulk feeders may also be prone to problems of over halogenation.

In order to better control the levels of halogen in existing bulk feeders the invention described herein includes a set of side by side cartridges that can be placed in fluid alignment in the open chamber of the prior art bulk feeders to allow an operator to more accurately control the level of halogen delivered to a body of water even though only one of the side by side cartridges may contain a halogen in puck or tablet form. As pointed out, one of the difficulties with bulk feeder systems that rely only on a halogen is that the level of halogen in the system must be maintained relatively high in order to ensure that the water is free of harmful organisms, which may result in the body of water having an annoying or obnoxious chlorine or bromine smell if the water is over halogenated.

One of the ways of lowering the level of the necessary halogen in a body of water is to use a two bactericide system that uses a secondary biocide material such as a source of metal ions in addition to the halogen which allows the halogen level to be maintained at a lower level since the two bactericides working together can effectively kill harmful microorganisms that would normally require a higher halogen level if only the halogen were present. The combination of the simultaneous delivery of two biocide can be effective in maintaining a system free of harmful organisms while at the same time reducing the obnoxious presence of high levels of halogens in the body of water. An example of a two-biocide or bactericide system is shown in my U.S. Pat. No. 6,527,952, which is hereby incorporated by reference. Unfortunately, such two bactericide systems require the homeowner to replace the bulk halogen feeder with a new inline cartridge feeder in order to properly dispense and maintain the lower halogen level since the bulk feeder controls and the open chamber in the bulk feeders are generally not well suited for maintaining low levels of halogen in the body of water.

The system described herein comprises a set of interacting side by side cartridges that can be placed in a chamber of a bulk feeder, which normally holds halogen in bulk form, to provide a cartridge system that can more precisely deliver at least two water treatment materials with the system including the ability to deliver halogen at a lower rate than halogen is normally delivered from a bulk feeder system. Consequently, the invention allows one to maintain a lower halogen level in the body of water allowing the system to be used with a second water treatment material. The use of an additional water treatment materials allows one to maintain the body of water in a safe condition using less halogen. In addition, no modifications to the bulk feeder are required since the cartridge system includes the ability to adjust and control the dispersant using the existing valve in the bulk feeder. For example, if a source of metal ions is used as a water treatment material and the second water treatment material is chlorine one can use the system described herein to deliver the first water treatment material while deliver the chlorine at a level sufficient to maintain the chlorine level at about 0.5 ppm or lower without modification of the bulk feeder.

Figure 3:
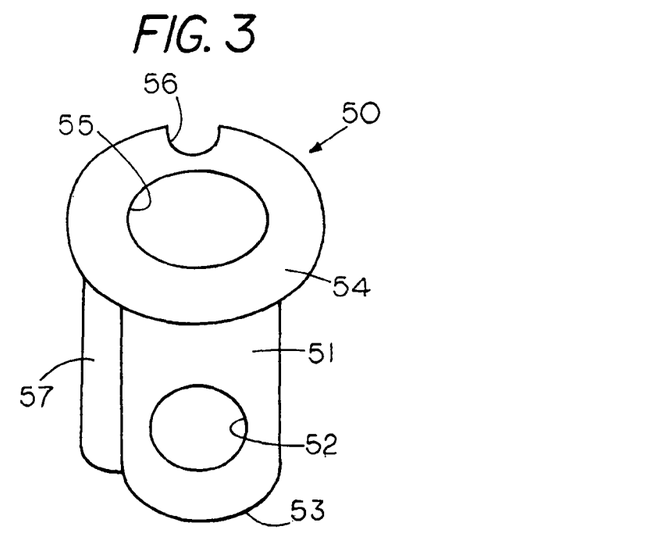
FIG. 3 shows a perspective view of a locater for holding a plurality of cartridges in an upright condition in a feeder.

FIG. 3 is a perspective view of a locater or holder 50 for maintaining a plurality of dispensing cartridges in an upright position or vertical orientation with a fluid port in each of the cartridges in fluid alignment with each other. By fluid alignment it is meant that the fluid flowing out of the outlet port of one of the cartridges flows into the inlet port of the other cartridge without circulating through the chamber in the bulk feeder. Holder 50 includes a cylindrical housing 51 having a lower edge 53 for engaging a bottom of a feeder and an inner cylindrical surface 55 having an opening 52 to provides for flow of water into a dispensing cartridge held within holder 50. A flange 54 extends radially outward from holder 50 to engage a side of the housing in a bulk feeder. Flange 54 may contain a feature such as a notch 56, which forms a locater that can be engaged with a feature of the bulk feeder to prevent rotation of the holder 50 with respect to the feeder. In addition when the locater 50 is in engagement with a feature of the bulk feeder the holder maintains the first cartridge and the second cartridge in a vertical orientation as well as holding the cartridges in a face to face condition to permit flow from one cartridge to the other cartridge without having the fluid circulate through the chamber of the bulk feeder. Thus the use of structural features on either the locator or the housing can be used to form a support for the dispensing cartridges described herein.

Extending lengthwise along housing 51 is a rib 57 that can be engaged with the side of a chamber of a bulk feeder to maintain the holder in an upright condition. Although only one rib is shown more or less ribs may be used depending on the type of bulk feeder. Thus a feature of the invention is that the holder 50 can convert an open chamber in a bulk feeder into a chamber where one can place dispensing cartridges therein with the dispensing cartridges maintainable in fluid alignment with each other and in an upright condition. In the example shown a flange and a rib are used to support the holder in a bulk feeder, however, due to the various designs of bulk feeders in some cases the flange may not be used and in other cases the ribs may not be used and in still other cases neither the flange or the ribs may be used. Likewise, although a single flange and a single rib have been shown multiple ribs or flanges may be used without departing from the spirit and scope of the invention.

Figure 4:
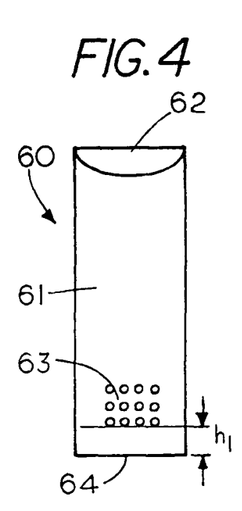
FIG. 4 is a front perspective view of a semi-cylindrical cartridge.

FIG. 4 is a front perspective view of an outer surface of a first elongated semi-cylindrical dispensing cartridge 60 having a closed top 62, a semi-cylindrical front face 61 with a fluid port 63 comprising a set of openings which are spaced at least a distance $h_1$ above the bottom 64 of dispensing cartridge 60 to thereby form a fluid accessible chamber therein for holding a water treatment material in a dispensing condition. The fluid port 63 is positioned a distance $h_1$ to receive fluid as it enters the chamber of a bulk feeder. In this example the location feature in the first dispensing cartridge is a bottom member 64 with the fluid outlet port 65 located at a fixed distance from a bottom of the bulk feeder and the location feature in the second dispensing cartridge is a bottom member 74 with the fluid inlet port 73 located at a fixed distance from the bottom member 74 of the bulk feeder.

Figure 5:
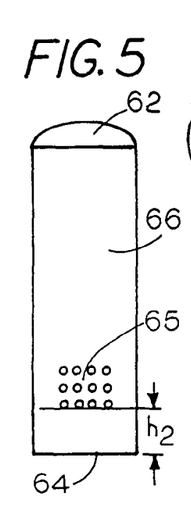
FIG. 5 is a rear perspective view of the semi-cylindrical cartridge of FIG. 4.

FIG. 5 is a rear perspective view of the semi-cylindrical elongated cartridge 60 of FIG. 4 revealing the planar back face 66 having a fluid port 65 comprising a set of openings which are located a least a distance $h_2$ above the bottom 64 of cartridge.

Figure 6:
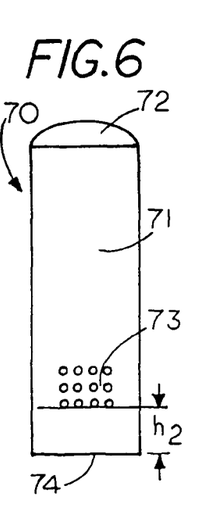
FIG. 6 is a front perspective view of a semi-cylindrical cartridge.

FIG. 6 is a rear perspective view of a second semi-cylindrical cartridge 70 having a planar face 71 for forming face-to-face engagement with the planar face 66 of semi-cylindrical cartridge 60 of FIGS. 4 and 5. Cartridge 70 includes a semi-cylindrical closed top 72, a closed bottom member 74 and a planar face 71, which contains a fluid port 73 comprising a set of openings that are located at least a distance $h_2$ above the bottom member 74 to form a dispensing cartridge with a chamber for holding a water treatment material therein. The fluid port 66 and the fluid port 73 are spaced the same distance $h_2$ above the bottom members so that when each of the cartridges 60 and 70 are supported from the bottom of the bulk feeder the fluid port 66 and fluid port 73 are in fluid alignment with each other to enable serial cartridge to cartridge flow when the cartridge 60 and 70 are in a face to face condition.

Figure 7:
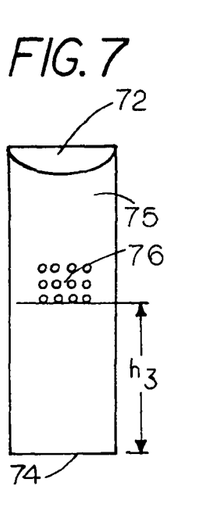
FIG. 7 is a rear perspective view of the semi-cylindrical cartridge of FIG. 6.

FIG. 7 is a front perspective view of the outer elongated semi-cylindrical cartridge of FIG. 6 revealing a semi-cylindrical front face 75 that includes a fluid port 76 comprising a set of openings 76 which are located at least a distance $h_4$ above bottom member 74. In this example port 76 comprises a fluid outlet port for directing fluid back into the main line. The function and the relationship of the dispensing cartridges will become more relevant with reference to bulk feeders of FIG. 8 and FIG. 9.

Figure 8:
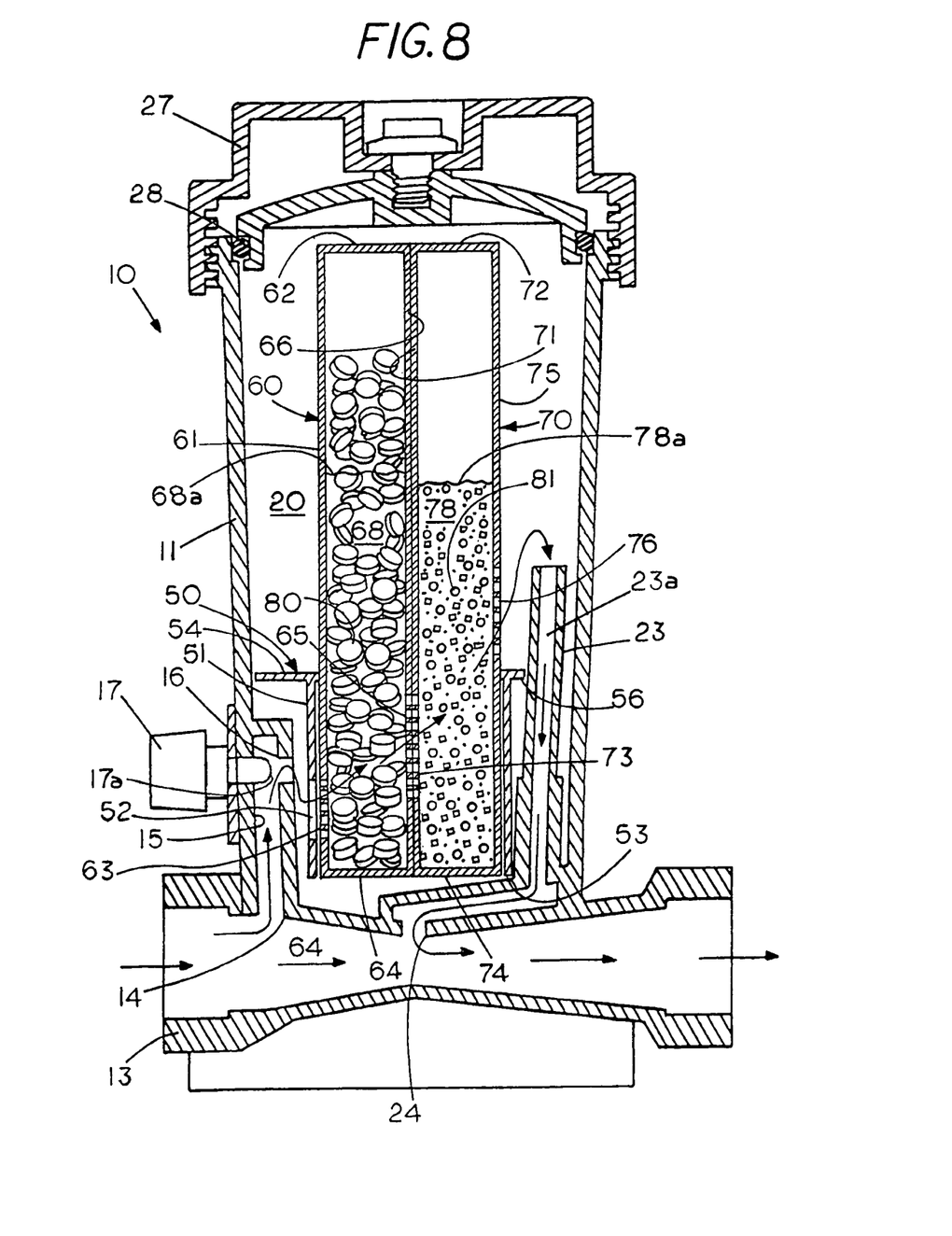
FIG. 8 is a sectional view of a bulk feeder with a pair of semi-cylindrical dispensing cartridges therein.

FIG. 8 is a sectional view of bulk feeder 10 of FIG. 1 with a pair of semi-cylindrical dispensing cartridges 60 and 70 held in a side-by-side condition by locator 50 with the feature of the planar face 66 of cartridge 60 in face-to-face engagement with the corresponding feature of planar face 71 of dispensing cartridge 70. In addition the feature of the cylindrical surfaces on cartridges 60 and 70 coact with the feature of the cylindrical surface or pocket 55 in locater 50 which can frictionally hold the dispensing cartridges 60 and 70 in a uniflow condition. That is, a condition where the fluid or water follows a serial torturous path through the dispensing material in both dispensing cartridges 60 and 70 before returning to the main line. When the dispensing cartridges are held in the face-to-face condition, as shown in FIG. 8, the fluid outlet port 65 of dispensing cartridge 60 is in fluid alignment with the fluid inlet port 73 of dispensing cartridge 70 so that fluid flowing through dispersing cartridge 60 flows directly into dispensing cartridge 70 before being allowed to be discharged from the bulk feeder. Consequently, the fluid, which in most cases is water, follows a serial cartridge-to-cartridge flow path once it enters inlet port 63.

In the example shown dispensing cartridge 60 includes a batch of halogen tablets or puck 80 which are stacked below and above the water line 68a of chamber 68. That is an air pocket exists at the top of chamber 68 since the top end 62 of cartridge 60 is closed so that air trapped therein does not escape from chamber 68. The size air pocket is a function of the back pressure in the system. Consequently, a portion of the tablets 80 remain above the water line 68a and in an undissolved or unused state until the tablets 80 below the water line erode and begin to dissolve, which allows the fresh tablets initially located above the water line to fall into the water in the lower portion of dispensing cartridge 60 to initiate the dissolution of the fresh tablets. This feature allows for extended delivery of the halogen since only a portion of the halogen tablets are in contact with the water in the dispensing cartridge during the initial dissolution of the halogen tablets.

In operation of the bulk feeder 10 with the dispensing cartridges 60 and 70 therein a portion of the fluid flowing through venturi housing 13 enters an inlet 14 and flows past the end 17a of valve 17 through opening 16 and through the opening 52 in holder 50 and into the fluid port 63 of dispensing cartridge 60. Rotation of valve 17 in one direction brings the end 17a closer to opening 16 thereby restricting the flow of fluid to the dispensing cartridges while rotation of valve 17 in the opposite direction increases the flow area through opening 16 by retracting the end 17a from opening 16.

The flow of fluid through the bulk feeder dispensing cartridge 60, which has a chamber 68 containing a halogen 80 such as chlorine or bromine in solid form with the chlorine or bromine in the shape of a puck or tablet. The chamber 68 includes a closed top 62 that forms an air pocket above the water line 69, which is the interface between the water and the air in chamber 68. In this example the water flows in through port 63, through the halogen tablets 80 in the lower portion of dispensing cartridge 60 and out the fluid port 65 of dispenser cartridge 60, which is in fluid alignment with the fluid port 73 of dispenser cartridge 70. Thus the fluid discharging from dispenser cartridge 60 flows directly into the water treatment materials comprising minerals 81, which are located in chamber 78 of dispenser cartridge 70. The water then flows out the fluid port 76 and into the stand pipe return passage 23a in standpipe 23. The water with the water treatment materials therein is returned to the housing 13 as indicated by the flow arrows.

The use of a plurality of two different water treatment dispensing cartridges located in series has been found to provide better and more precise dispensing control of the dispersants than from the bulk feeder without the two dispensing cartridges. The improved control has been found to occur without having to modify or change the control valves on the bulk feeder or without having to exchange the bulk feeder for an inline feeder. That is, the dispensing cartridges can be placed in a serial cartridge-to-cartridge flow condition in the bulk feeder to reduce the delivery rate of dispersants therefrom without the need for structural changes within the bulk feeder. Thus, a device which delivers poor control of a single dispersant when used for its intended purpose as a bulk feeder can deliver more precise control of delivery rates and at lower delivery rates when two or more dispensing cartridges are located in series within the bulk feeder. A feature of the invention is that one obtains better control of the delivery rate and can also deliver a halogen at a lower rate by placing the two dispersants in series so that the water flows in a serial manner through both the water treatment materials before being discharged from the bulk feeder.

Figure 9:
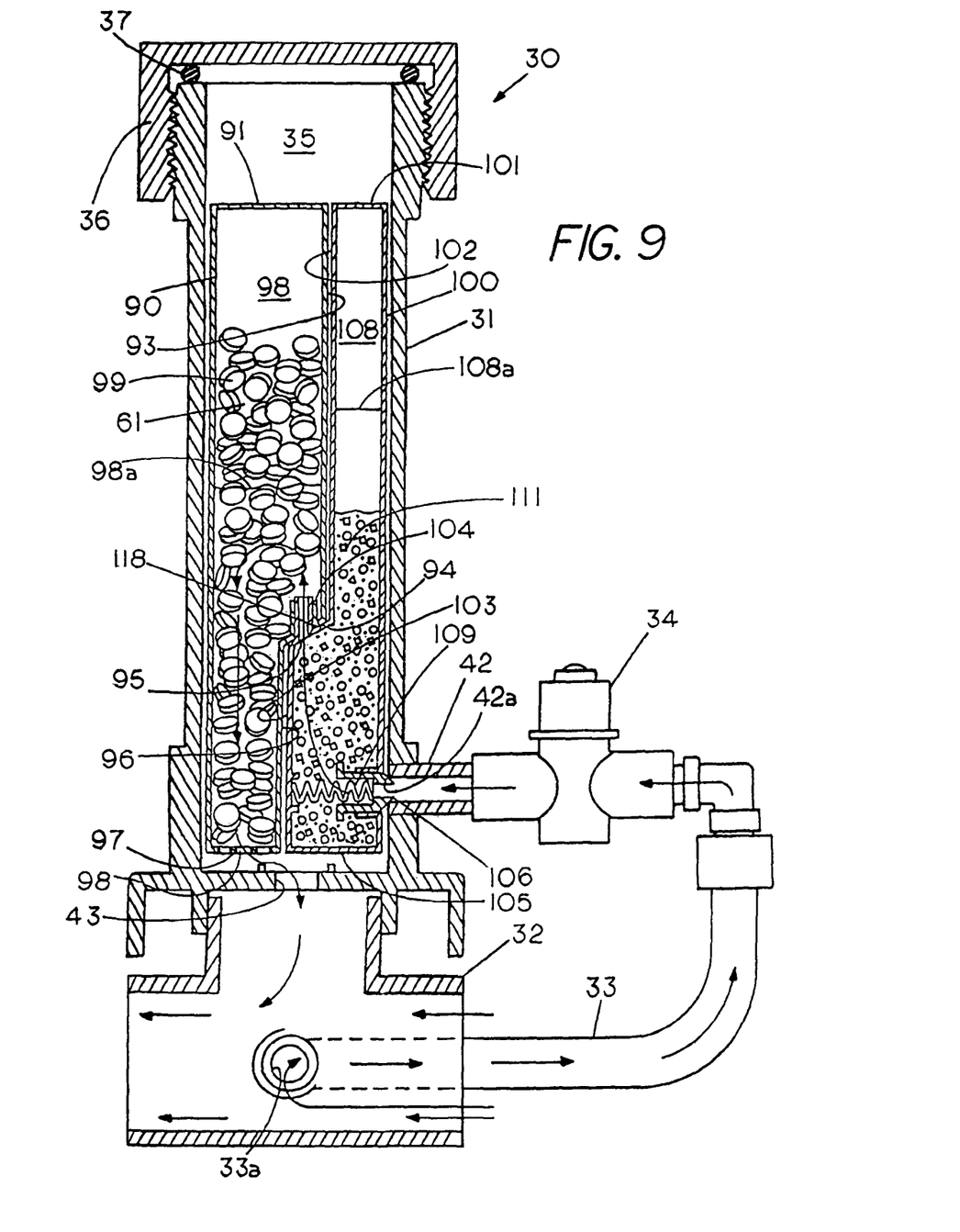
FIG. 9 is a sectional view of a bulk feeder with a pair of interlocked dispensing cartridges.
Figure 10:
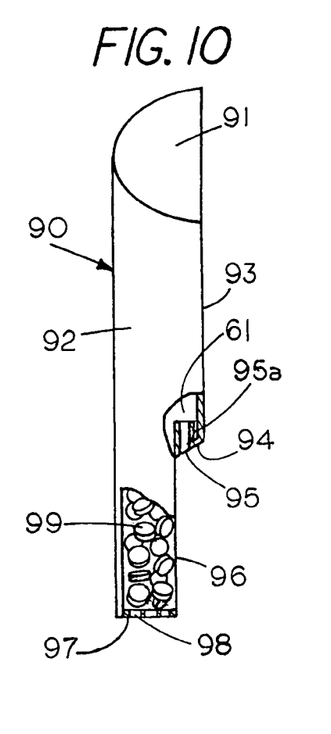
FIG. 10 is a partial sectional view of a dispensing cartridge.
Figure 11:
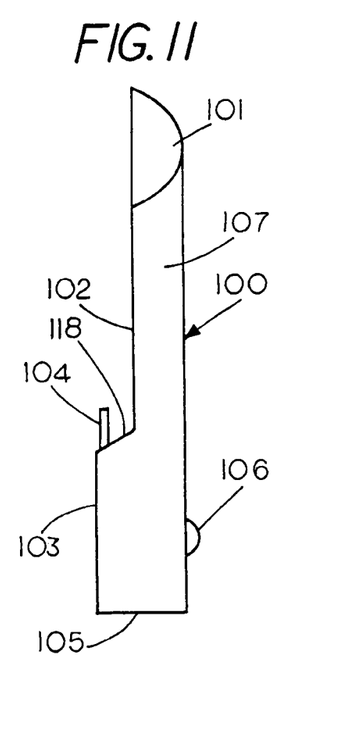
FIG. 11 is a perspective view of a dispensing cartridge that interlocks with the dispensing cartridge of FIG. 10.

FIG. 9 is a sectional view of an example of another type of cylindrical shaped bulk feeder 30 with a pair of interlocked elongated dispensing cartridges 90 and 100 located in a face-to-face condition therein while FIG. 10 shows an isolated partial sectional view of a first interlocking dispensing cartridge 90 and FIG. 11 shows an isolated perspective view of a second interlocking dispensing cartridge 100. In cartridge 90 and 100 the elongated configuration of the cartridges forms a feature for maintaining a static orientation of the cartridges in an upright condition in the chamber of the feeder while the faces and the interlocking spout forms further features for maintaining the cartridges in a serial flow condition.

As shown in FIG. 10 the first interlocking dispensing cartridge 90 has an elongated side member comprising a semi-cylindrical front face 92, a side member having a planar face 93, a second side member having a planar face 96, which is offset inwardly from planar face 93 by an intermediate side member having a planar face 94. A top semi-cylindrical shaped member 91 forms a closed end to the top of cartridge 90. A bottom member 97 includes a fluid port 98 which contains a plurality of openings therein large enough for passage of fluid therethrough but sufficiently small to prevent halogen tablets 99 from falling therethrough. The intermediate planar face 94 connects planar face 93 to planar face 96 with planar face 94 having an inlet tube 95 with a sidewall 95a with the tube 95 extending upward into a chamber 98 in dispensing cartridge 90 with tube 95 forming a locater or feature for engagement with locater spout or feature 104 on cartridge 100.

FIG. 11 shows the second mateable dispensing cartridge 100 includes a top member 101 and a bottom member 105 with a first side member 107 having a semi-cylindrical shape. Cartridge 100 includes a side member having a planar face 102 and a side member having a planar face 103 that is offset from planar face 102. An intermediate side member having a planar face 118 connects planar face 103 to planar face 102 with intermediate planar face 118 containing a locater comprising an extension spout 104 for forming interlocking engagement with a locater in cartridge 90 as well as for forming a fluid path between the side-by-side cartridges 90 and 100. In this example the feature or locater in cartridge 90 comprises the inlet tube 95, which is located in the dispensing cartridge 90. An outer semi-cylindrical face 107 extends from end to end of dispensing cartridges and connects planar face 103 and planar 102 to form a chamber therein. A top member 101 and a bottom member 105 form end closures for cartridge 100. A resiliently mounted fluid inlet collar 106, which extends radially outward from semi-cylindrical face 107, forms a feature or locater for maintaining a fixed rotational orientation of cartridge 100 with respect to a feature 42a of the bulk feeder as well as to form a fluid inlet passage for flow of fluid into the compartment within dispenser cartridge 100.

FIG. 9 shows the dispensing cartridge 90 and dispenser cartridge 100 located in face-to-face mating engagement within a cylindrical compartment 35 of bulk feeder 30. In this condition the face 93 of cartridge 90 and the face 102 of cartridge as well as face 96 of cartridge 90 and face 103 of cartridge 100 are in a face-to-face condition. In addition the spout 104 is positioned within tube 95 to interconnect the chamber 108 of cartridge 100 with the chamber 98 of cartridge 90 to provide a flow path between the dispensing cartridges 90 and 100. In addition spout 104 and tube 95 each provide features that maintain the cartridges 90 and 100 in fluid communication with each other as well as in interlocking engagement with each other. In the example of FIG. 9 a first biocide 111 comprises a mineral and the second biocide 99 comprises a halogen in puck or tablet form with the second cartridge 90 including an air pocket above the water line 98a for maintaining a portion of the halogen 99 above the water line in an unwetted condition during an initial portion of a dispensing cycle. That is, until the tablets 99 below the water line 98a dissolve the tablets 99 above the water line 98a will remain dry. Once the tablets below the water line disperse the tablets above the water line fall down to replace the tablets or pucks that have been consumed. Although a water pocket has been used in some cases one may elect not to use an air pocket and allow the water to contact all the tablets or pucks once water flows through the feeder.

Cylindrical compartment 35 of bulk feeder 30, when used as a bulk feeder, normally holds solid halogen tablets or pucks, which are dissolved and eroded as the water flows through the chamber (see FIG. 2). Bulk feeder 30 includes a cap 36 for providing access to chamber 35 and a ring seal 37 to prevent fluid from escaping from feeder 30 when the bulk feeder 30 is in use. In operation of bulk feeder 30 in the non-bulk mode as shown in FIG. 9, i.e. with mateable dispensing cartridges 90 and 100 therein, a portion of fluid from the housing 32 flows through inlet port 33a and into tube 33. A valve 34 allows one to control the flow of fluid through a central opening in inlet collar 106. In the example shown a spring 109 resiliently maintains inlet collar 106 in engagement with a feature of the housing, which in this example comprises the rim or circular edge 42a of inlet tube 42 to enable fluid flow through the inlet collar 106, spring 109 and into the dispensing material 111, which is located in chamber 108. Typically dispensing material 111 comprises a water treatment material such as a source of metal ions such as silver ions, which for example may be silver chloride although other sources of ions may be used without departing from the spirit and scope of the invention.

The fluid entering chamber 108 flows upward through the dispensable material 111 but remains outside the air pocket located above the water line 108a, which is the interface between the water and the air in dispensing cartridge 100. For the fluid to escape from dispenser cartridge 100 the fluid flows through tube 104 and into the chamber 98 in dispensing cartridge 90. Dispensing cartridge 90 includes a closed top section enabling the formation of an air pocket that extends to the water line 98a. In the example shown a portion of the halogen tablets or pucks 99 are located above the water line 98a and remain in a dry state. As the halogen tablets below the water line are consumed the halogen tablets located above the water line 98a fall into the water and are consumed. Thus fresh halogens tablets can be automatically replenish those halogen tablets below the water line that are continually being consumed by the presence of water flowing therethrough.

In the example shown in FIG. 9 the two dispensing cartridges 90 and 100 have been placed in series in the chamber 35 of the bulk feeder which normally only holds solid halogen tablets to provide serial flow from cartridge to cartridge. The placement of the two dispensing cartridges 90 and 100 in series enables one to dispense two different water treatment materials at the same time and at a lesser rate than if only a single dispersant where present in the chamber 35 of the bulk feeder. It also provides enhanced control of the delivery of the water treatment materials without alteration to the valve controls 34. Consequently, the invention eliminates problems of over halogenation in bulk feeders when bulk halogen tablets are placed in the open chamber in the bulk feeder Which allow the bulk feeder to be used with a two biocide system where the level of the halogen is considerably lower than if only a halogen is used as a biocide.

A feature of the invention is a method of converting a bulk feeder to a serial cartridge system thorough the use of cartridges that are positioned to maintain serial fluid flow through adjacent cartridges with the flow rate controlled by the existing valve control on the bulk feeder. For example, with respect to FIG. 9 the invention includes a method of converting a bulk feeder having an inlet 42 and an outlet 43 to a serial cartridge system by placing a first elongated cartridge 100 having first face 105 with a fluid outlet port 104 in a portion of a chamber in the bulk feeder 30; placing a second elongated cartridge 90 having a mating face and a fluid inlet port 95 in a face to face condition with the first elongated condition cartridge wherein the fluid outlet port 104 and the fluid inlet port 95 are in fluid alignment with each other and the cartridges 90 and 100 engaging a locater or inlet collar 106 with a feature 42a of the bulk feeder 30 to maintain the first elongated cartridge 100 and the second elongated cartridge 90 in fluid alignment therebetween and in series with each other which enables one to direct a serial flow of fluid into and out of the bulk feeder 30 by serially flowing the fluid into the first elongated cartridge 100 and out of the second elongated cartridge 90 before discharging the fluid from the bulk feeder. From the examples shown the dispending cartridges system can utilize a structural feature or features of the dispensing cartridges or a structural feature of the bulk feeder or both to maintain the fluid dispensing cartridges in a serial side-by-side dispensing condition. While certain structural features have been identified for holding the cartridges in position other structural features of either the dispensing cartridges or the bulk feeder may be used as a location feature without departing from the spirit and scope of the invention.

Similarly, with respect to FIG. 8 the invention includes a method of converting a bulk feeder having an inlet 16 and an outlet 23 to a serial cartridge system by placing a first elongated cartridge 60 having a feature such as a first face 66 with a fluid outlet port 65 in a portion of a chamber in the bulk feeder 10, placing a second elongated cartridge 70 having a feature such as a mating face 71 and a fluid inlet port 66 in a face to face condition with the first elongated cartridge 60 wherein the fluid outlet port 104 and the fluid inlet port 95 are in fluid alignment with each other and the cartridges 90 and 100 engaging a feature such as a locater 50 with a feature such as stand pipe 23 of the bulk feeder 10 to maintain the first elongated cartridge 60 and the second elongated cartridge 70 in fluid alignment therebetween and in series with each other to direct a serial flow of fluid into and out of the bulk feeder 10 by serially flowing the fluid into the first elongated cartridge 60 and out of the second elongated cartridge 70.

In each of the systems the method may include the step of placing a batch of chlorine or bromine in one of the cartridges and a source of metal ions such as silver ions in the form of silver chloride in the other cartridge. The method may further include the step of directing the water in the bulk feeder into a bottom inlet of a first elongated cartridge 60 and back into a main line through an outlet 76 located in a second elongated cartridge. A feature of the system with the set of dispensing cartridges is that the cartridges change the fluid dynamics within the chamber in the bulk feeder, which allows one to use an existing control valve on the bulk feeder to maintain the chlorine levels at levels not normally attainable with bulk feeders. For example the valve on the bulk feeder 17 or 34 can be adjusted to maintain a chlorine level at about 0.5 ppm or lower when the first elongated cartridge and the second elongated cartridge are located in a side by condition in the bulk feeder.

Figure 12:
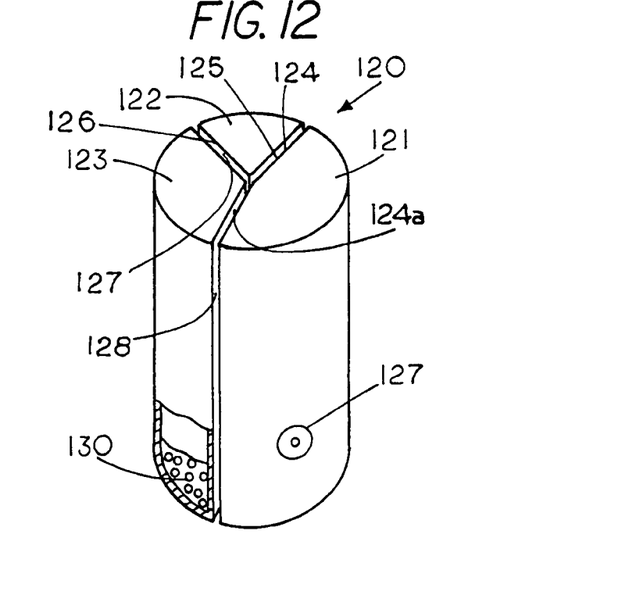
FIG. 12 is a perspective view of a three separate dispensing cartridge.

While the system has been described with respect to use of two dispensing cartridges located in a serial flow condition in some cases one may want to deliver three or more water treatment materials. The dispensing cartridge system described herein is well suited for such a task. FIG. 12 is a perspective view of a further example of a plurality of dispensing cartridges 120 that shows three separate elongated dispensing cartridge 121, 122 and 123 with each of the cartridges having a pie shape to form a cylindrical configuration when the cartridges are placed in a face-to-face condition with each other. That is cartridge 121 has a planar face 124 and 124a with planer face 124 located in face-to-face engagement with face 125 and planar face 124a located in face-to-face engagement with face 128 of dispensing cartridge 123. Similarly, face 127 of dispensing cartridge 123 is located in face-to-face condition with face 126 of dispensing cartridge 122. In this example an inlet fluid port 127 is located in dispensing cartridges 120. Each of the dispensing cartridges 121, 122 and 123 include pathways therebetween to enable water to flow successively through each of the three dispensing cartridge. An outlet 130 for returning the dispersants to the stream may be located on the bottom member of the dispensing cartridge 123 to enable fluid communication from cartridge to cartridges and from the cartridge to the return stream through a set of lateral fluid ports as shown in FIGS. 4-7, which are located in fluid alignment with each other. In this example, the first cartridge 121 and the second cartridge 122 are each located in a face to face condition with the third cartridge 123 which has an outlet port 130 for directing fluid away from the cartridges and the first cartridge 121 includes a fluid inlet 107 for directing fluid into the serially arranged cartridges. While the multiple cartridges are shown with pie shaped configuration other configuration of the dispensers which provide serial flow through at least two of the cartridges may be used without departing from the spirit and scope of the invention.

FIG. 2A shows a swimming pool 38 using an existing bulk feeder 30, which contains two or more cartridges connected to a pool circulation system comprising pipe 46, pump 39 and pipe 42 with the output side of bulk feeder 30 connected to pool 38 through pipe 48. In this example no system changes are needed to deliver two or more materials.

We claim:

1. A side-by-side cartridge system for reducing over chlorination in a bulk feeder having a single dispensing chamber and a control valve comprising:
    a first cartridge containing a water treatment material therein, said first cartridge having a at least two side members with at least one of the two side members having an outlet port for flow of a liquid therethrough while preventing passage of the water treatment material therethrough;
    a second cartridge containing a water treatment material, said second cartridge having at least two side members with at least one of the two side members having an inlet port for flow of a liquid therethrough while preventing passage of the water treatment material therein from passing therethrough, and
    a locater for engaging a feature of the bulk feeder, said locater having a cartridge compartment for holding said first cartridge and said second cartridge in a static side-by-side condition with the fluid outlet port of the first cartridge in fluid alignment with the fluid inlet port in the second cartridge to thereby provide a direct cartridge to cartridge serial flow of the water through both of the dispensing cartridges when the first cartridge and the second cartridge are located in a chamber of the bulk feeder.

2. The cartridge system of claim 1 wherein the locater is in engagement with a feature of the bulk feeder to maintain the first cartridge and the second cartridge in a vertical orientation and an inlet port of the first cartridge is held in fluid communication with an inlet of the bulk feeder to enable the control valve on the bulk feeder to control the flow of water through the first cartridge and the second cartridge.

3. The cartridge system of claim 1 wherein the locater includes a cylindrical chamber and a feature for forming a non-rotational engagement with a feature of the bulk feeder.

4. The cartridge system of claim 1 wherein the second cartridge includes a fluid outlet port and a chamber located above said fluid outlet port for trapping air therein to maintain at least a portion of a halogen in a non-wetted condition above a water line therein during an initial portion of a water treatment cycle.

5. The cartridge system of claim 4 wherein at least one of the water treatment materials comprises a batch of minerals that includes silver chloride.

6. A cartridge system for a feeder comprising:
    a first cartridge containing a biocide therein, said first cartridge having a feature for maintaining a static orientation of the first cartridge in a bulk feeder and a fluid port for flow of a liquid therethrough while preventing passage of solids therethrough; and
    a second cartridge containing a second biocide, said second cartridge having a locater, said second cartridge having an inlet for ingress of fluid therein with the feature of the first cartridge and the locater of the second cartridge engageable with each other for maintaining the fluid port of the first cartridge in fluid alignment with the fluid port of the second cartridge when the second cartridge is located in a first face to face condition with the first cartridge to thereby provide a cartridge to cartridge flow path therebetween.

7. The cartridge system of claim 6 including a third dispensing cartridge wherein each of the cartridges contains a water treatment material different from each of the other dispensing cartridges.

8. The cartridge system of claim 6 wherein each of the dispensing cartridges have a semi cylindrical shape and each have a planar face with a fluid port therein in wherein the fluid port in the planar face of each of the dispensing cartridges are in fluid alignment with each other.

9. The cartridge system of claim 6 including a holder having a locater to maintain the first cartridge and the second cartridge in a fixed condition with respect to each other.

10. A system for converting a bulk feeder system to a multiple cartridge system comprising:
    an inline bulk feeder having a chamber therein for normally holding a halogen in tablet or puck form in a free condition therein;
    a bulk feeder valve for control of a water flow into the chamber of the bulk feeder;
    a first dispensing cartridge having a fluid outlet port and a location feature with said first dispending cartridge positionable in an upright condition in a portion of said chamber, said first dispensing cartridge occupying less than an entire volume of the chamber; and
    a second dispensing cartridge having a fluid inlet port and a location feature with said second dispensing cartridge positionable in a further portion of said chamber with said location feature of said second dispensing cartridge and said location feature of said first dispensing cartridge maintaining the fluid outlet port of said first dispensing cartridge in a fluid alignment with the fluid inlet port of said second dispensing cartridge to provide cartridge to cartridge flow of water between the first dispensing cartridge and the second dispensing cartridge before the water is discharged from the inline bulk feeder.

11. The system of claim 10 including a third cartridge containing a water treatment material wherein the first cartridge contains a source of metal ions and the second cartridge contains a batch of halogen.

12. The system of claim 10 wherein the location feature in the first dispensing cartridge is a bottom member for holding the fluid outlet port at a fixed distance from a bottom of the bulk feeder and the location feature in the second dispensing cartridge is a bottom member for holding the fluid inlet port at the fixed distance from the bottom of the bulk feeder.

13. A cartridge system for placement in fluid series in an inline bulk feeder comprising:
    a first cartridge having an elongated chamber for holding and dispensing a first biocide therefrom, said first cartridge having a location feature and a fluid outlet port for flow of fluid from said first cartridge; and
    a second cartridge having a chamber therein for holding a second biocide in solid form therein, said second cartridge having a location feature and a inlet fluid port with the location feature of the first cartridge and the location feature of the second cartridge maintaining the outlet of the second cartridge in fluid alignment with the fluid inlet port of second cartridge to provide cartridge to cartridge flow of water therebetween.

14. The cartridge system of claim 13 wherein the location feature of the first cartridge includes a spout for engaging the location feature in the second cartridge.

15. The cartridge system of claim 13 wherein said first cartridge and said second cartridge each include a planar face with the second cartridge and the first cartridge located in a face to face condition with an exterior surface of the first cartridge and an exterior surface of the second cartridge each having a cylindrical shape for positioning within a cylindrical chamber of a bulk feeder.

16. The cartridge system of claim 13 wherein said first cartridge includes a resiliently mounted inlet collar for maintaining a fixed rotational orientation of the first cartridge with respect to a feature of the bulk feeder.

17. The cartridge system of claim 13 wherein the first cartridge includes a mineral and the second cartridge includes a halogen in tablet form with said second cartridge including an air pocket for maintaining a portion of the halogen in an unwetted condition during an initial portion of a dispensing cycle.

18. The cartridge system of claim 13 including a third cartridge wherein the first cartridge and the second cartridges are located in a face to face condition with the third cartridge having an outlet port for directing fluid therefrom and the first cartridge includes a fluid inlet for directing fluid through said first cartridge said second cartridge and said third cartridge.

19. The method of converting a bulk feeder having an inlet and an outlet to a serial cartridge system comprising:
    placing a first elongated cartridge having first face with a fluid outlet port in a portion of a chamber in the bulk feeder;
    placing a second elongated cartridge having a mating face and a fluid inlet port in a face to face condition with the first elongated cartridge wherein the fluid outlet port and the fluid inlet port are in fluid alignment with each other; and
    engaging a feature of the bulk feeder with at least one of the elongated cartridges to maintain the first elongated cartridge and the second elongated cartridge in fluid alignment therebetween and in a serial flow condition with each other; and
    directing a serial flow of fluid into the first elongated cartridge and out of the second elongated cartridge when the first elongated cartridge and the second elongated cartridges are located in a side-by-side condition in a chamber of the bulk feeder.

20. The method of claim 19 wherein the first elongated cartridge and the second elongated cartridge are frictional mounted in the locater.

21. The method of claim 19 including the step of placing a batch of chlorine or bromine in the second cartridge and a source of silver chloride in the first cartridge.

22. The method of claim 19 including the step of directing the water in the bulk feeder into a bottom inlet of the first elongated cartridge and back into a main line through an outlet located in the second elongated cartridge.

23. The method of claim 21 including adjusting a valve on the bulk feeder to maintain the chlorine at about 0.5 ppm or lower when the first elongated cartridge and the second elongated cartridge are located in a side by condition in the bulk feeder.

24. A cartridge system comprising a plurality of cartridges for placement in a serial flow condition in a chamber of an inline feeder comprising:
    a first cartridge having a chamber for holding and dispensing a first water treatment material therefrom with said first cartridge having a fluid inlet port and a fluid outlet port;
    a second cartridge positionable in a face-to-face condition with said first cartridge, said second cartridge having an elongated chamber therein for holding a second water treatment material, said second cartridge having a fluid inlet port in fluid alignment with the fluid outlet port in said first cartridge to thereby form a serial flow of fluid from said first cartable to said second cartridge without the fluid flowing into the chamber in the inline feeder wherein the first cartridge and the second cartridge each have feature having a feature for maintaining the fluid outlet port of first cartridge and the fluid inlet port of the second cartridge in fluid alignment with each other when both are present in the face-to-face condition in an inline feeder.

25. The cartridge system of claim 24 including a third cartridge said third cartridge having a chamber therein for holding a third water treatment material therein and a feature for maintaining the third cartridge in fluid alignment with at least one of the other cartridge.

26. The cartridge system of claim 24 wherein each of the cartridges includes a feature for maintaining each of the cartridges in fluid alignment at least one of the cartridges includes a closed top for maintenance of an air pocket therein.

* * * * *